United States Patent [19]
Chauhan

[11] Patent Number: 5,613,980
[45] Date of Patent: Mar. 25, 1997

[54] BIFURCATED CATHETER SYSTEM AND METHOD

[76] Inventor: Tusharsindhu C. Chauhan, 242 Michael Dr., Uniontown, Pa. 15401

[21] Appl. No.: 361,976

[22] Filed: Dec. 22, 1994

[51] Int. Cl.$^6$ ................................................ A61M 29/00
[52] U.S. Cl. .......................... 606/194; 128/898; 604/98
[58] Field of Search ...................... 604/96–104; 606/159, 606/190, 191–198; 128/898

[56] References Cited

U.S. PATENT DOCUMENTS

| | | |
|---|---|---|
| 3,993,078 | 11/1976 | Bergentz et al. . |
| 4,195,637 | 4/1980 | Grüntzig et al. . |
| 4,413,989 | 11/1983 | Schjeldahl et al. . |
| 4,896,670 | 1/1990 | Crittenden . |
| 4,994,071 | 2/1991 | MacGregor . |
| 5,129,883 | 7/1992 | Black . |
| 5,143,093 | 9/1992 | Sahota . |
| 5,197,951 | 3/1993 | Mahurkar . |

OTHER PUBLICATIONS

Medical Progress–Percutaneous Transluminal Coronary Angioplasty, by Landau et al., The New England Journal of Medicine, pp. 981–993—Apr. 7, 1994.

*Primary Examiner*—Glenn Dawson
*Attorney, Agent, or Firm*—Selitto & Associates

[57] ABSTRACT

A catheter system adapted for dilating a preselected stenosed region of a blood vessel having a first branch and a second branch includes an inflatable member having a first branch portion and a second branch portion. In use, the inflatable member is inserted into the blood vessel and routed to the stenosed region through the blood vessel. The first portion and the second portion are positioned in the first branch and the second branch, respectively, and then inflated, whereby the vessel is dilated facilitating blood flow therethrough. The first and second portions of the member may be inflated simultaneously.

31 Claims, 10 Drawing Sheets

BIFURCATED CATHETER SYSTEM AND METHOD

FIELD OF THE INVENTION

The present invention relates to medical devices and procedures and, more particularly, to a catheter system and a method adapted for dilating and closing hollow spaces and passages, such as blood vessels.

BACKGROUND OF THE INVENTION

Catheters have been employed in a variety of medical procedures (see, e.g., U.S. Pat. No. 4,994,071) and, in particular, in percutaneous transluminal coronary angioplasty (PTCA). As an alternative to a coronary arterial bypass surgery, PTCA is a procedure for treating a patient having an occlusion or stenosis of a coronary artery. In performing PTCA, a catheter is introduced to an occluded region of the artery, and an expander (i.e., balloon) attached to the catheter is then inflated within the region to dilate the artery's luminal passage, thereby improving blood flow through the artery.

An occlusion at or about a bifurcated region of an artery presents a special problem in performing a PTCA procedure at such a region because dilating a branch artery may cause closure of an adjacent branch artery. Further, dilating a trunk artery may "snow plow" plaque in the trunk artery into one or both of the branch arteries causing an occlusion therein.

Various catheters and methods have been developed in treating occlusions at or about a bifurcated region of an artery. For instance, U.S. Pat. No. 4,896,670 discloses a kissing balloon catheter technique utilizing a pair of balloon catheters which are simultaneously inflated while each catheter is positioned in one of branch arteries. Although this technique prevents the closure of one branch artery while the other branch is dilated, the trunk artery may not be dilated sufficiently to treat stenosis therein due to a narrow proximal end design of the balloon catheters.

U.S. Pat. No. 4,413,989 discloses a catheter having a bifurcated balloon which includes a pair of branches. With one branch wrapped around the other branch, the balloon, in a deflated state, is routed along a guidewire through an artery to a bifurcated region, at which a PTCA operation is to be performed. With both branches of the balloon positioned in a first branch artery of the region, the wrapped branch is positioned in a second branch artery by inflating the balloon. More particularly, as the balloon is inflated, the wrapped branch expands and pops out of the first branch artery and into the second branch artery. Because the wrapped branch is not positioned in the second branch artery prior to the inflation of the balloon, there is a risk of damaging the walls of the arteries when the second branch pops out of the first branch artery and into the second branch artery. Further, as the balloon is inflated, the wrapped branch may kink, thereby inhibiting it from properly popping into the second branch artery. Such a kink may cause many complications including the prolongation of the time during which blood supply to distal blood vessels is obstructed by the inflated catheter. Such an obstruction of blood flow is detrimental to the heart and may cause arrythmia (i.e., electric disturbance in the heart), which can lead to permanent heart damage.

SUMMARY OF THE INVENTION

The present invention overcomes the disadvantages and shortcomings of the prior art devices discussed above by providing a new and improved catheter system adapted for quickly introducing it to a preselected stenosed region of a blood vessel having a first branch vessel and a second branch vessel and efficiently and effectively dilating the stenosed region. More particularly, the catheter system includes an inflatable member having a first branch portion and a second branch portion. In use, the inflatable member is inserted into the blood vessel and routed to the stenosed region through the blood vessel. The first portion and the second portion are positioned in the first branch vessel and the second branch vessel, respectively, and then inflated, whereby the vessel is dilated facilitating blood flow therethrough. The first and second portions of the inflatable member may be inflated simultaneously. Alternatively, they may be independently and selectively inflated.

BRIEF DESCRIPTION OF THE DRAWINGS

For a better understanding of the present invention, reference is made to the following description of various exemplary embodiments of the invention considered in conjunction with the accompanying drawings in which.

DETAILED DESCRIPTION OF THE EXEMPLARY EMBODIMENTS

Although the present invention can be used to perform various types of medical procedures, it is particularly suitable for use in performing a PTCA operation. Accordingly, the present invention will be described hereinafter in connection with such a medical procedure. It should be understood, however, that the following description is only meant to be illustrative of the present invention and is not meant to limit the scope of the present invention which has applicability to medical procedures other than a PTCA operation.

Figure 1:
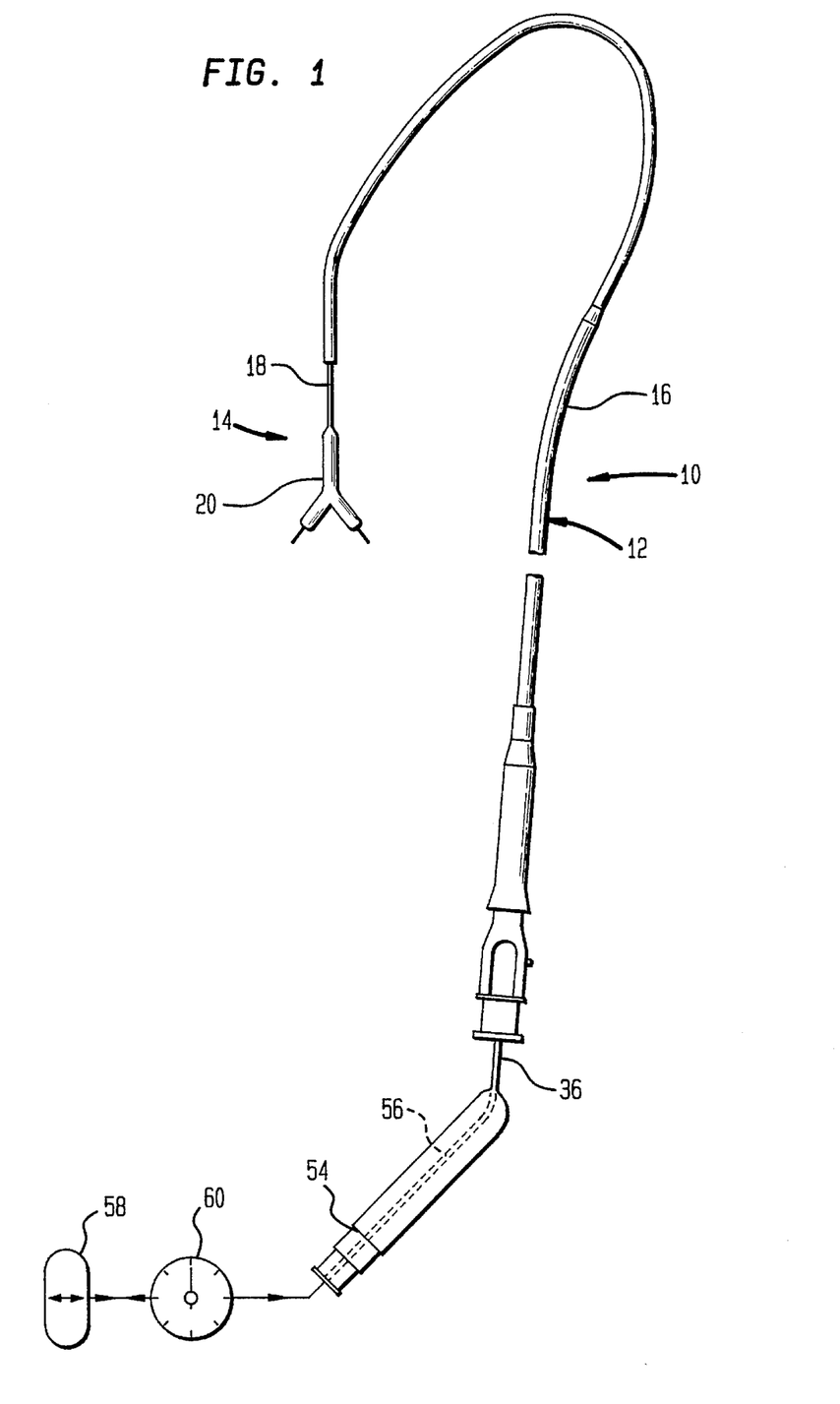
FIG. 1 is a schematic illustration of a catheter system constructed in accordance with a first embodiment of the present invention.
Figure 2:
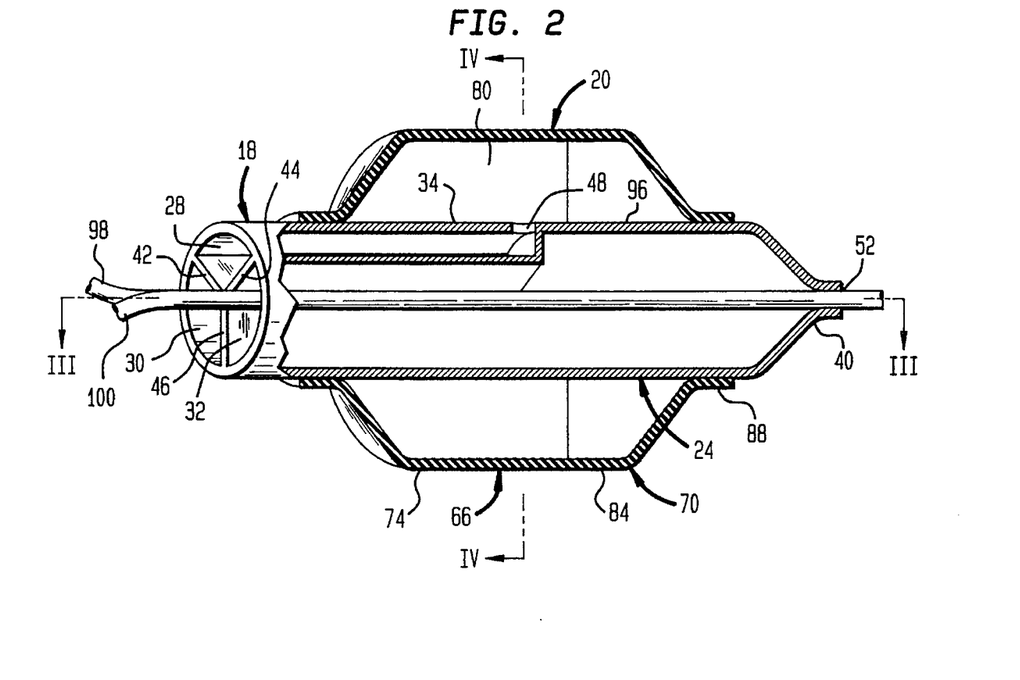
FIG. 2 is a partial cross-sectional view of a dilating catheter employed by the system shown in FIG. 1, the dilating catheter being shown in an inflated state.
Figure 3:
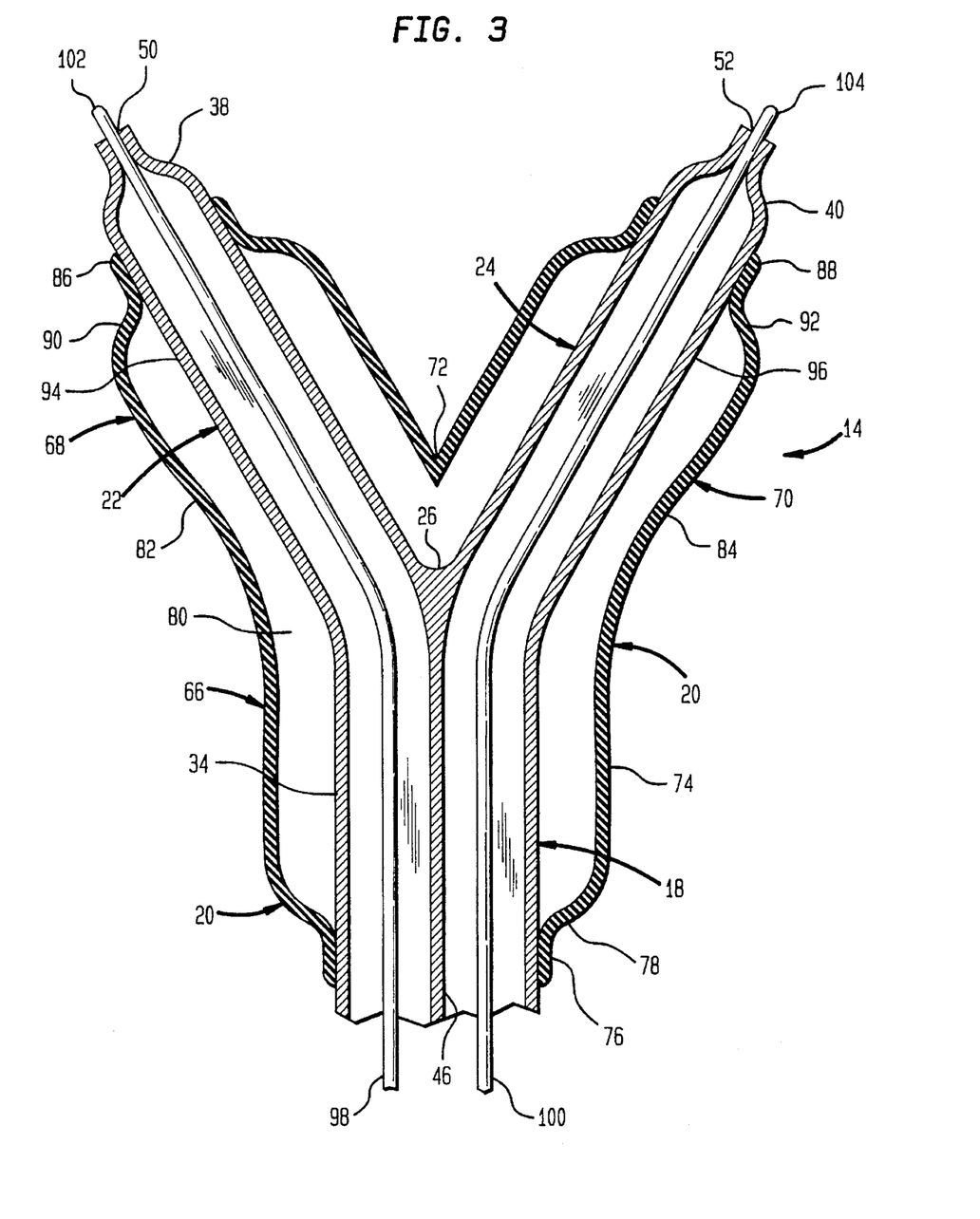
FIG. 3 is a cross-sectional view, taken along section line III—III of FIG. 2 and looking in the direction of the arrows, of the dilating catheter shown in FIG. 2.
Figure 4:
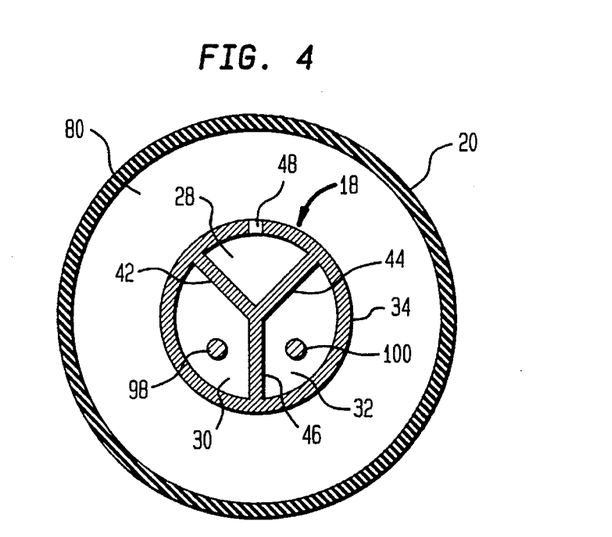
FIG. 4 is a cross-sectional view, take along line IV—IV of FIG. 2 and looking in the direction of the arrows, of the dilating catheter shown in FIG. 2.

Referring to FIGS. 1–4 but primarily to FIG. 1, a catheter system 10 includes a guide catheter 12 and a dilating catheter 14 inserted into an elongated guide hose 16 of the guide catheter 12. The dilating catheter 14 includes an elongated carrier tube 18 arid a bifurcated dilating element 20 (i.e. an expander), which is also referred to herein as an inflatable balloon and which is attached in a pressure-tight manner to the carrier tube 18. With particular reference to FIG. 3, the carrier tube 18 includes a pair of branch extensions 22, 24 pivotally connected to the carrier tube 18 at a bifurcating region 26 of the carrier tube 18, which also includes lumens 28, 30, 32 enclosed by a circumferential wall 34 of the carrier tube 18 (see FIGS. 2 and 4). More particularly and with reference to FIGS. 2–4, the lumen 28 extends through the carrier tube 18 from a proximate end 36 (see FIG. 1) of the carrier tube 18 to the bifurcating region 26 (see FIG. 3) of the carrier tube 18. The lumens 30, 32 extend through the carrier tube 18 from the proximate end 36 to distal ends 38, 40, respectively, of the branch extensions 22, 24, respectively. The lumen 28 is divided from the lumens 30, 32 by dividers 42, 44 respectively, extending along the entire length of the lumen 28 and enclosing a distal end of the lumen 28 at the bifurcating region 26 (see FIG. 3) such that the lumen 28 is sealed from the lumens 30, 32 along its entire length and forms a passageway for pressurized fluid for purposes to be discussed hereinafter. Likewise, the lumens 30, 32 are divided from each other by a divider 46 extending from the proximate end 36 to the bifurcating region 26 (see FIG. 3) such that the lumens 30, 32 are sealed from each other along their entire length. The circumferential wall 34 of the carrier tube 18 includes an opening 48 adjacent to the bifurcating region 26 (see FIG. 3) of the carrier tube 18, the opening 48 communicating with the lumen 28 for purposes to be discusses hereinafter. Alternatively, the opening 48 may be positioned on the circumferential wall 34 remote from the bifurcating region 26. The distal ends 38, 40 of the branch extensions 22, 24, respectively, include apertures 50, 52, respectively, (see FIGS. 2 and 3) communicating with the lumens 30, 32, respectively, for purposes to be discusses hereinafter. Referring again to FIG. 1, the proximal end 36 of the carrier tube 18 is attached to a connector 54 having a channel 56 communicating with the lumen 28 in a pressure-tight manner. The channel 56 is connected to a pump 58 via a pressure measuring device 60 for purposes to be discusses hereinafter.

Referring to FIGS. 2 and 3, the balloon 20, which has a unitary construction, includes a trunk section 66 and a pair of branch sections 68, 70 pivotally connected to the trunk section 66 at a bifurcation point 72 of the balloon 20. When inflated, the trunk section 66 has a substantially cylindrical wall 74 of a diameter which is larger than the diameter of the circumferential wall 34 of the carrier tube 18. The trunk section 66 also includes a collar 76 at a proximate end 78 of the balloon 20, the collar 76 being connected to the circumferential wall 34 of the carrier tube 20 in a pressure-tight manner, thereby forming a space 80 between the trunk section 66 and the carrier tube 18, the space 80 being in communication with the opening 48. Likewise, the branch sections 68, 70 include substantially cylindrical walls 82, 84, respectively, each having a diameter, when inflated, which is larger than its corresponding branch extension 22, 24. The branch sections 68, 70 also include collars 86, 88, respectively, at distal ends 90, 92, respectively, thereof. The collar 86 is attached to a circumferential wall 94 of the branch extension 22 in a pressure-tight manner, thereby forming a continuum of the space 80 between the branch extension 22 and the branch section 68. Similarly, the collar 88 is attached to a circumferential wall 96 of the branch extension 24 in a pressure-tight manner, thereby forming a continuum of the spade 80 between the branch extension 24 and the branch section 70.

The catheter system 10 also includes a pair of flexible guidewires 98, 100 extending through the lumens 30, 32, respectively, of the carrier tube 18. The guidewires 98, 100 have round distal ends 102, 104 which extend through the apertures 50, 52, respectively, of the branch extensions, 22, 24, respectively.

Figure 5:
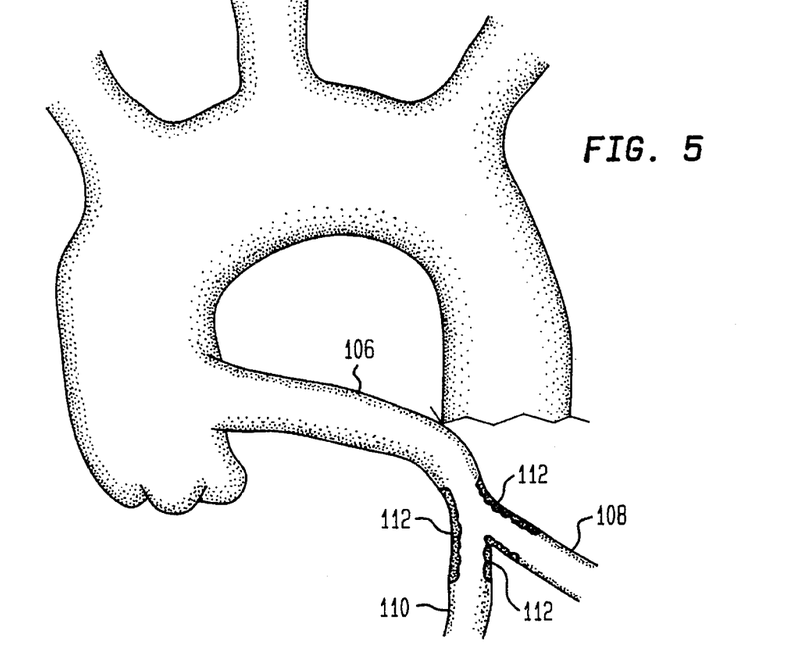
FIG. 5 is a schematic illustration of a coronary artery having a stenosed region at which a PTCA operation is to be performed.
Figure 6:
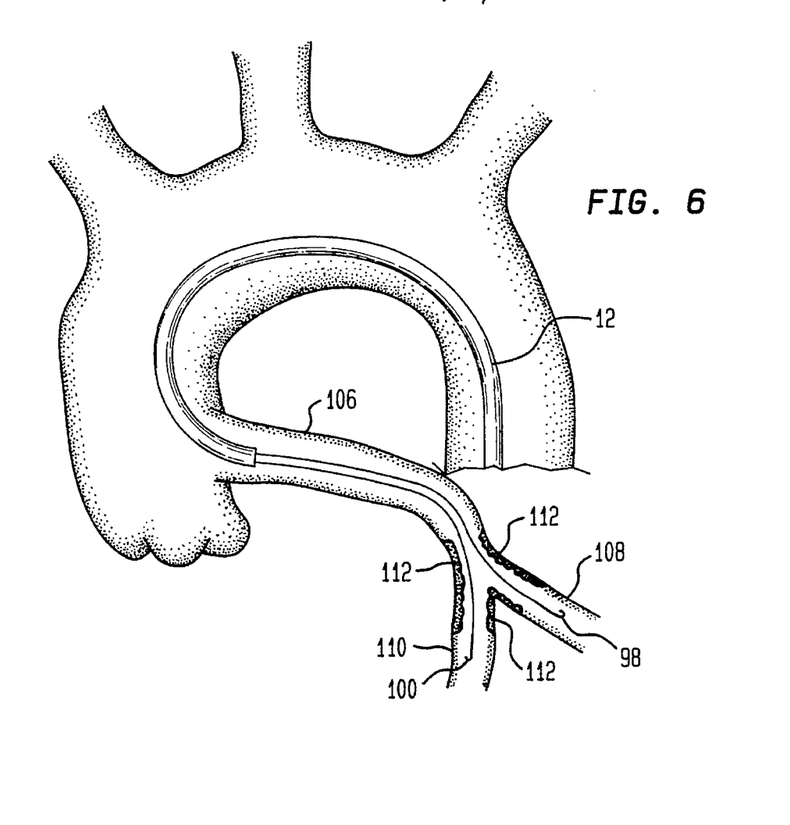
FIG. 6 shows, in a schematic fashion, how two guide wires employed by the system of FIG. 1 is positioned in the artery shown in FIG. 5.
Figure 7:
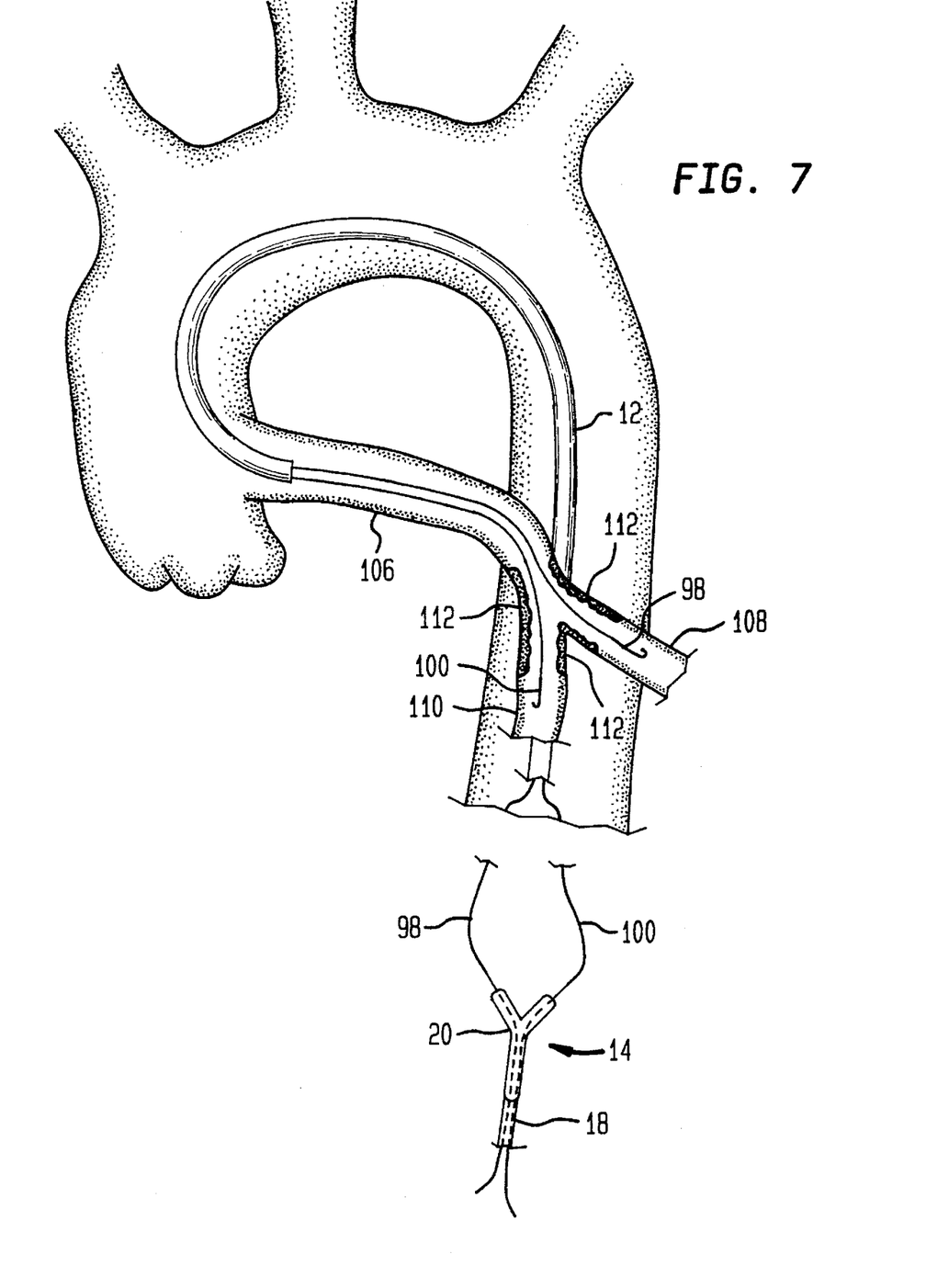
FIG. 7 shows, in a schematic fashion, how the dilating catheter of FIG. 2 is routed to the stenosed region shown in FIG. 5.
Figure 8:
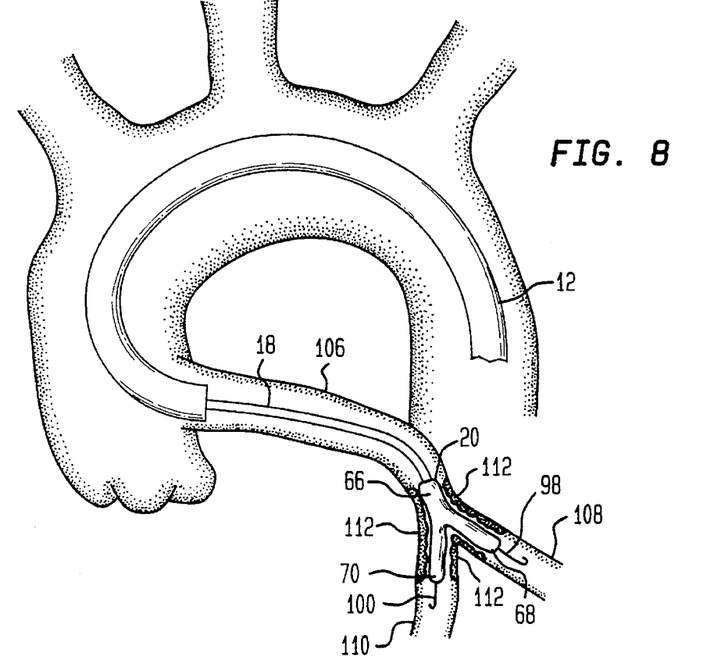
FIG. 8 shows, in a schematic fashion, how the dilating catheter of FIG. 2 is positioned within the stenosed region shown in FIG. 5, the dilating catheter being shown in a deflated state.

FIG. 5 shows a left main coronary artery 106 splitting into a left circumflex branch 108 and a left anterior descending branch 110, the artery 106 and the branches 108, 110 being narrowed by plaques 112 accumulated within the artery 106 and the branches 108, 110. In performing a PTCA procedure at the stenosed region shown in FIG. 5, the guide catheter 12 is inserted into a femoral artery (not shown) or, in the alternative, into another blood vessel, which is well known in the art, by the Seldinger technique or other conventional methods and is advanced to the ostium of the artery 106 to be dilated. The guidewires 98, 100 are advanced through the guide catheter 12 and routed through the artery 106 and through branch vessels 108, 110, respectively, by a conventional method which is well known in the prior art (see FIG. 6). With the distal ends 102, 104 of the guidewires 98, 100, respectively, extending across the stenosis in the branches 108, 110, proximal ends of the guidewires 98, 100 are inserted into the lumens 30, 32, respectively, of the carrier tube 18 through the apertures 50, 52 (see FIG. 7). Next, with the balloon 20 in a deflated state, the dilating catheter 14 is routed to the stenosed region through the guide catheter 12, and is then positioned within the stenosed region with the help of the guidewires 98, 100. More particularly, the branch sections 68, 70 of the balloon 20 are independently and simultaneously positioned within the stenosed segments of the branches 108, 110, respectively, guided by the guidewires 98, 100, respectively, while the trunk section 66 of the balloon 20 is positioned within the stenosed segment of the artery 106 (see FIG. 8).

Figure 9:
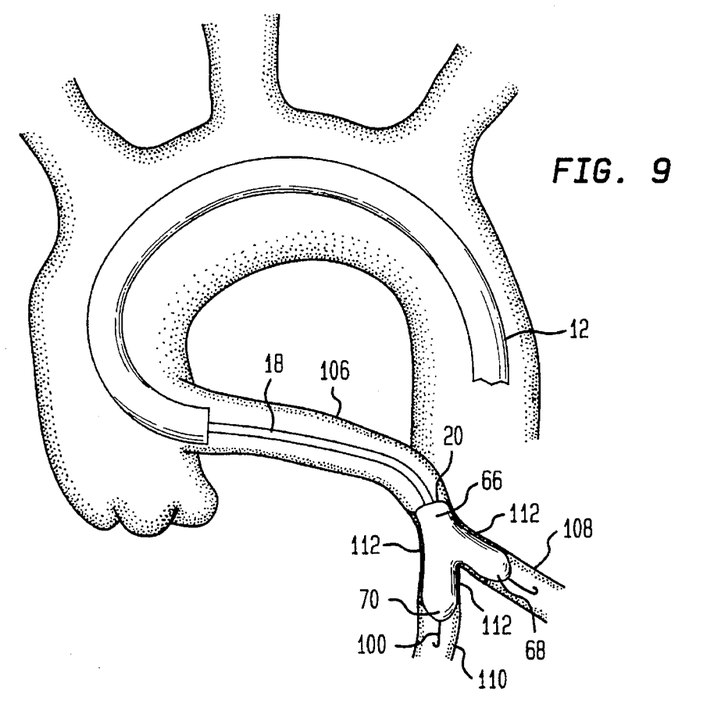
FIG. 9 is similar to FIG. 8 except that the dilating catheter is shown in an inflated state.
Figure 10:
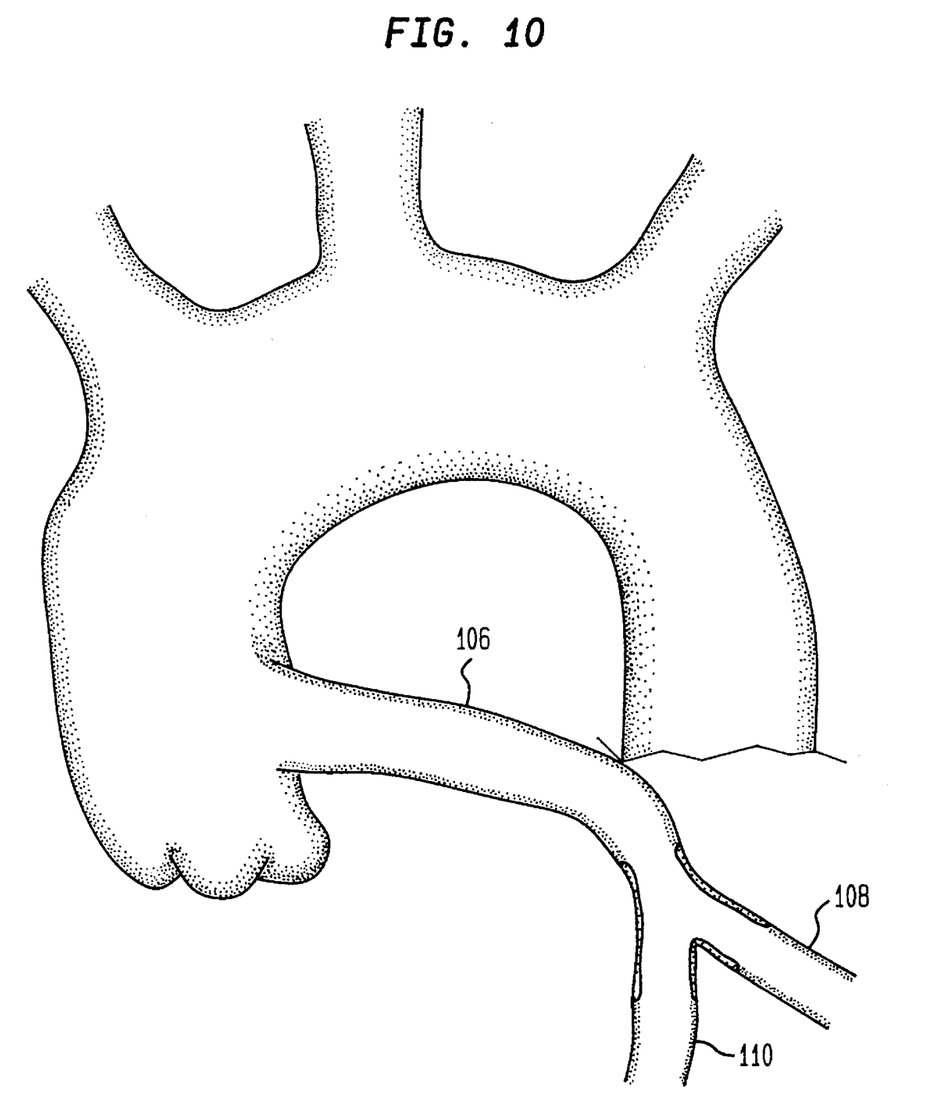
FIG. 10 shows the stenosed region of FIG. 5 after the performance of a PTCA operation and the removal of the dilating catheter of FIG. 2 from the stenosed region.

The trunk section 66 and branch sections 68, 70 of the balloon 20 are then simultaneously inflated by conveying pressurized fluid to the space 80 formed between the carrier tube 18 and the balloon 20. More particularly, pressurized fluid is delivered from the pump 58 to the space 80 through the lumen 28 via the opening 48. Alternatively, the inflation of the balloon 20 can be achieved and/or supplemented by other conventional methods, such as a dilating method utilizing a heater probe or a laser. As the trunk section 66 and branch sections 68, 70 of the balloon 20 are inflated to their predetermined sizes for a predetermined time, which is well known in the art, and at a predetermined pressure, which is also well known in the art, the artery 106 and the branches 108, 110 are dilated (see FIG. 9). If it is determined that the artery 106 and the branches 108, 110 are not fully dilated to allow a sufficient blood flow therethrough, the dilation step shown in FIG. 9 can be repeated with the prepositioned dilating catheter 14 or, in the alternative, with a different dilating catheter whose balloon has a size and/or shape which are different from the size and shape of the prepositioned balloon 20. After the artery 106 and the branches 108, 110 are fully dilated allowing a sufficient blood flow therethrough, the guide catheter 12, the guidewires 98, 100 and the dilating catheter 14 are removed from the stenosed region (see FIG. 10).

It should be appreciated: that the present invention provides an effective and safe system and method adapted for performing a PTCA procedure at a bifurcated stenosed region of a blood circulation system. Because the artery 106 and the branches 108, 110 are simultaneously dilated, the danger of causing inadvertent closure of either branches 108, 110 and a "snow plowing" effect is minimized. Further, because the branch sections 68, 70 are properly placed in their corresponding branch vessels before the inflation of the balloon 20, a PTCA procedure can be expeditiously performed without kinking of the branch sections 68, 70. In addition, because the branch extensions 22, 24 and the branch sections 68, 70 are pivotally connected to the carrier tube 18 and the balloon 20, respectively, it should also be appreciated that the catheter system 10 is adapted for use in performing angioplasty procedures at bifurcating vessels having different bifurcating angles (i.e., angles between bifurcating branch vessels) which may be less than, equal to or greater than 90 degrees.

It should be understood that the catheter system 10 and the steps of using the catheter system 10 as discussed hereinabove in conjunction with FIGS. 5–10 can have many variations ant modifications. For instance, the guide catheter 12 may be omitted or can be replaced by any conventional means and, consequently, the step of inserting the guide catheter 12 through the femoral artery may be omitted or replaced by other conventional methods. The catheter system 10 may also include a conventional perfusion mechanism for providing a continuous blood supply to a distal blood vessel. Moreover, the configuration of the lumens 28, 30, 32 extending through the carrier tube 18 may vary. For example, instead of providing separate lumens corresponding to each of the guidewires 98, 100, the carrier tube 18 may be provided with a single lumen for providing a passageway for both of the guidewires 98, 100. The balloon 20 may also be attached to the carrier tube 18 by any conventional means or may be removably attached to the carrier tube 18 so that it can be replaced with another balloon having a different shape and size. The branch extensions 22, 24 of the carrier tube 18 and the branch sections 68, 70 of the balloon 20 may be fixedly attached to the carrier tube 18 and the balloon 20, respectively. In this way, the bifurcation angle between the branch extensions 22, 24 and the branch sections 68, 70 can be adjusted to match the bifurcation angle between preselected bifurcating vessels. In addition, the shapes and the sizes, such as the diameters and the lengths, of the trunk section 66 and the branch sections 68, 70 of the balloon 20 may be different from each other, the sizes and shapes being predetermined by the size and shape of the vessels at a preselected bifurcated portion of the blood circulatory system at which an angioplasty procedure is to be performed. Likewise, the number of the branch extensions 22, 24, the branch sections 68, 70 and the guidewires 98, 100 are predetermined by the number of branching vessels at a preselected portion of the blood circulatory system at which an angioplasty procedure is to be performed. For instance, if the preselected portion has three branches, the catheter 10 would also have three branch extensions, three branch sections and three guidewires.

Concerning potential applications for the catheter system 10, it should be understood that the catheter system 10 of the present invention is adapted for use in performing an angioplasty procedure at other parts of a coronary artery as well as at other blood vessels, such as the popliteal, femoral, carotid and aortic arteries. The system 10 can also be used in performing a temporary closure of blood vessels to cause a temporary obstruction of a blood flow therethrough by inflating the balloon 20 (see FIG. 9). In addition, the dilation and closure of hollow tubular passages other than blood vessels, such as a biliary tree, can be achieved using the system 10. Further, the system 10 is adapted for use in carrying out perfusion of blood and/or medicine to a predetermined section of blood vessels.

Figure 15:
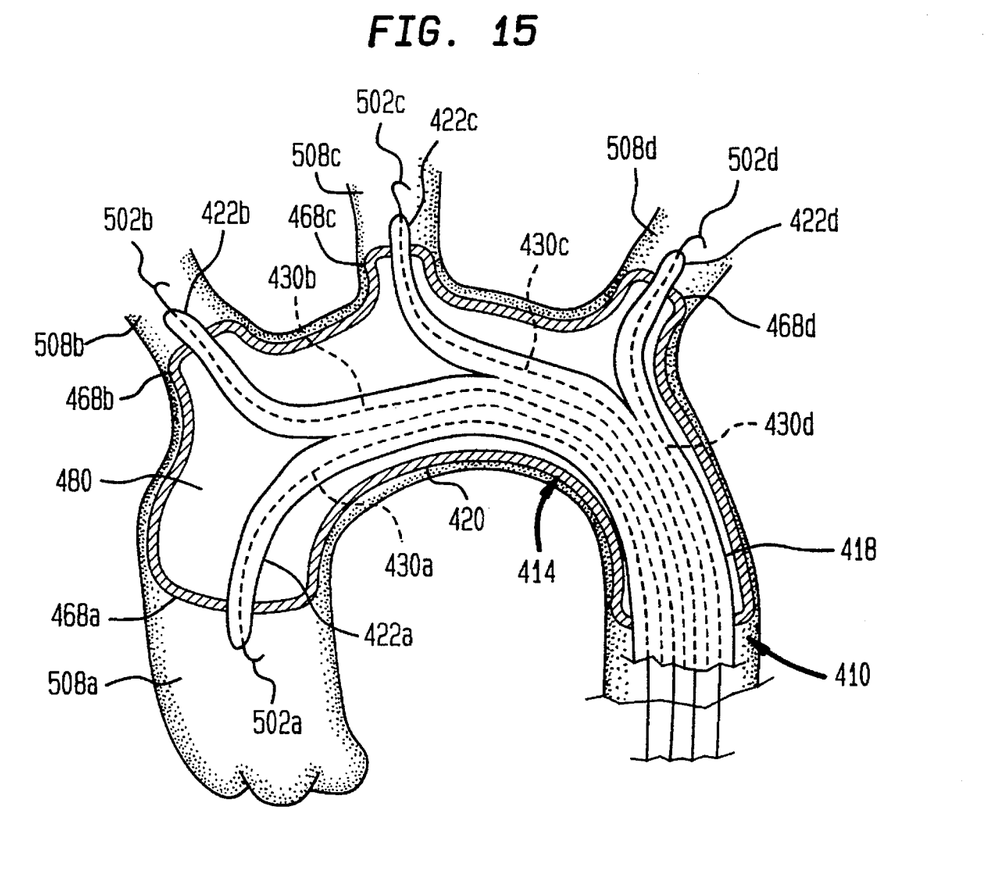
FIG. 15 is a schematic illustration of a catheter system constructed in accordance with a third embodiment of the present invention, a dilating catheter employed by the system being positioned within a stenosed region of an arch of an aorta and being in an inflated state.

FIGS. 11–14 and FIG. 15 depict a second embodiment and a third embodiment, respectively, of the present invention. The embodiment of FIGS. 11–14 and the embodiment of FIG. 15 are constructed and used in the same manner as the embodiment of FIGS. 1–5 unless it is otherwise stated. Accordingly, in FIGS. 11–14 and in FIG. 15, a numbering convention is employed wherein elements shown therein having a function or structure in common with a counterpart in previously discussed FIGS. 1–5 are given the same number incremented by two hundred and four hundred, respectively.

Referring to FIGS. 11–14, an elongated carrier tube 218 of a dilating catheter 214 of a catheter system 210 includes four lumens 228a, 228b, 230, 232 enclosed by a circumferential wall 234 of the carrier tube 218. More particularly and with particular reference to FIGS. 12 and 14, the lumens 228a, 228b extend through the carrier tube 218 from a proximate end 236 (see FIG. 11) of the carrier tube 218 to distal ends 238, 240, respectively, of the branch extensions 222, 224 (see FIG. 13), respectively, of the carrier tube 218. Likewise, the lumens 230, 232 extend through the carrier tube 218 from the proximate end 236 (see FIG. 11) of the carrier tube 218 to the distal ends 238, 240 (see FIG. 13), respectively, of the branch extensions 222, 224. The lumen 228a is divided from the lumens 228b, 230, 232 by dividers 242, 312 extending along the entire length of the lumen 228a such that the lumen 228a is sealed from the lumens 228b, 230, 232 along its entire length and forms a passageway for pressurized fluid. Likewise, the lumen 228b is divided from the lumens 228a, 230, 232 by the divider 312 and a divider 244 extending along the entire length of the lumen 228b such that the lumen 228b is sealed from the lumens 228a, 230, 232 along its entire length and forms a passageway for pressurized fluid. Similarly, the lumens 230, 232 are divided from each other by a divider 246 extending from the proximate end 236 of the carrier tube 218 to a bifurcating region 226 (see FIG. 13) of the carrier tube 218 such that the lumens 230, 232 are sealed from each other along their entire length. An opening 248a, which is positioned on the circumferential wall 234 of the carrier tube 218, communicates with the lumen 228a; while an opening 248b, which is positioned on a circumferential wall 296 of the branch extension 224, communicates with the lumen 228b for purposes to be discusses hereinafter.

Figure 11:
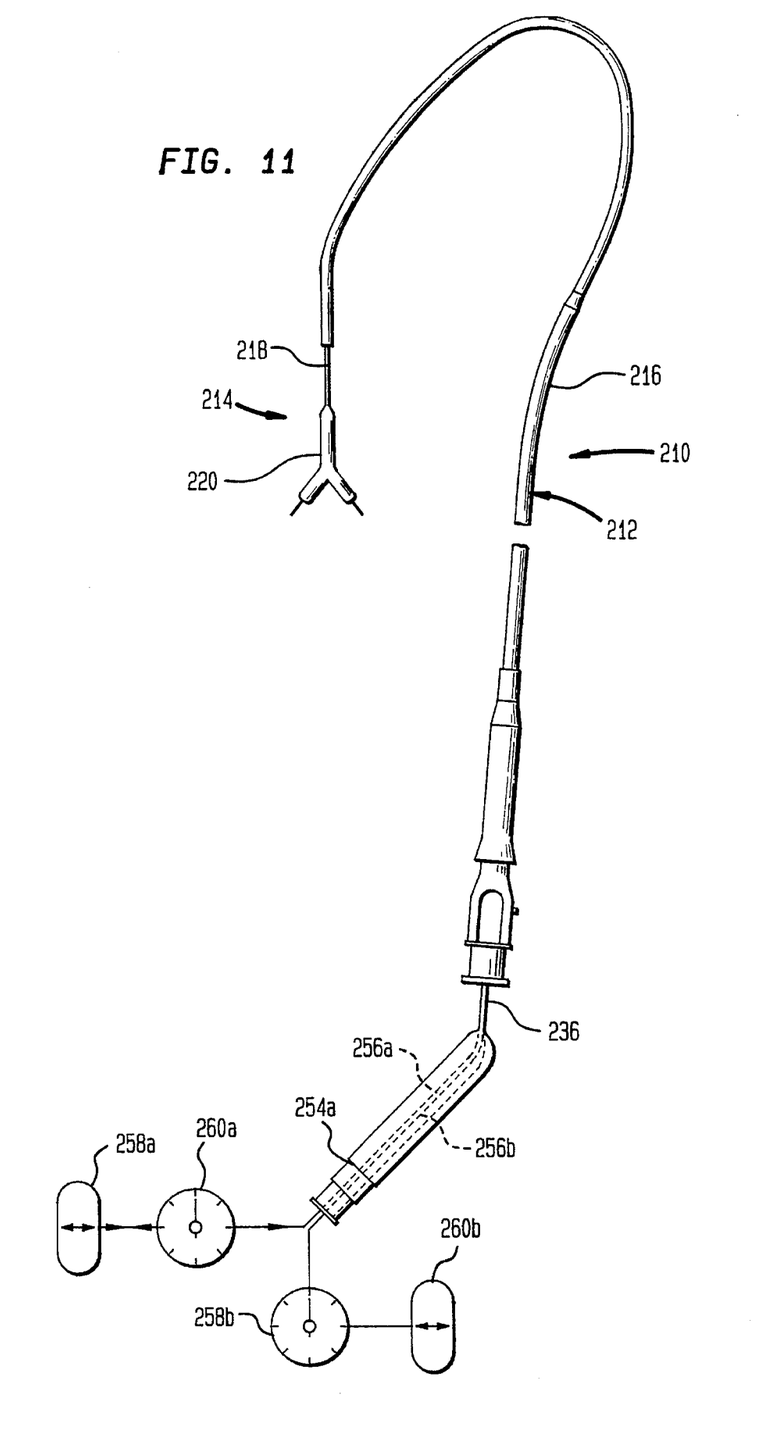
FIG. 11 is a schematic illustration of a catheter system constructed in accordance with a second embodiment of the present invention.
Figure 12:
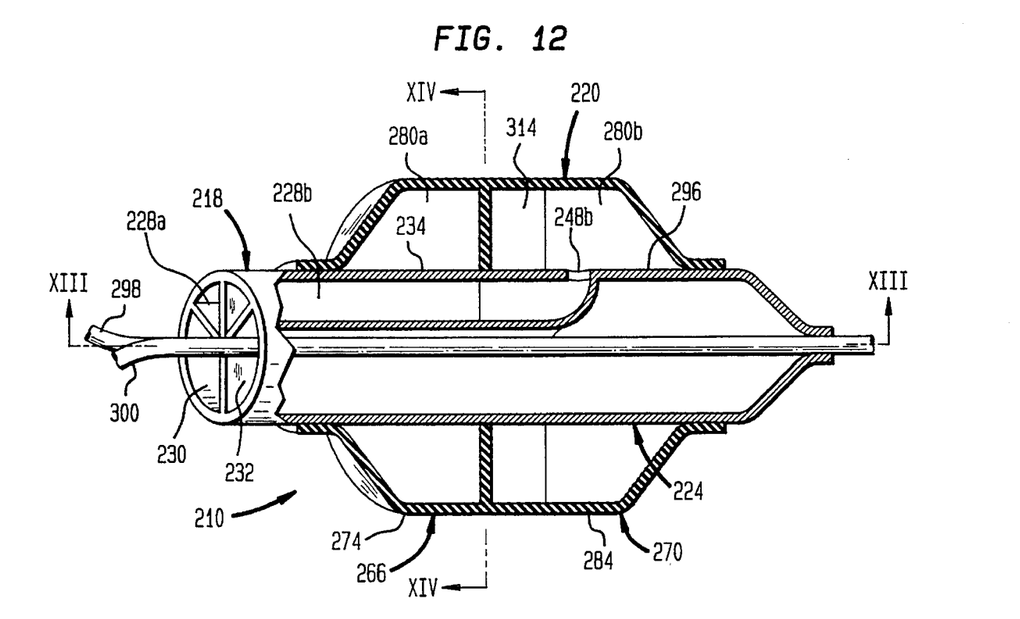
FIG. 12 is a partial cross-sectional view of a dilating catheter employed by the system shown in FIG. 11, the dilating catheter being shown in an inflated state.
Figure 13:
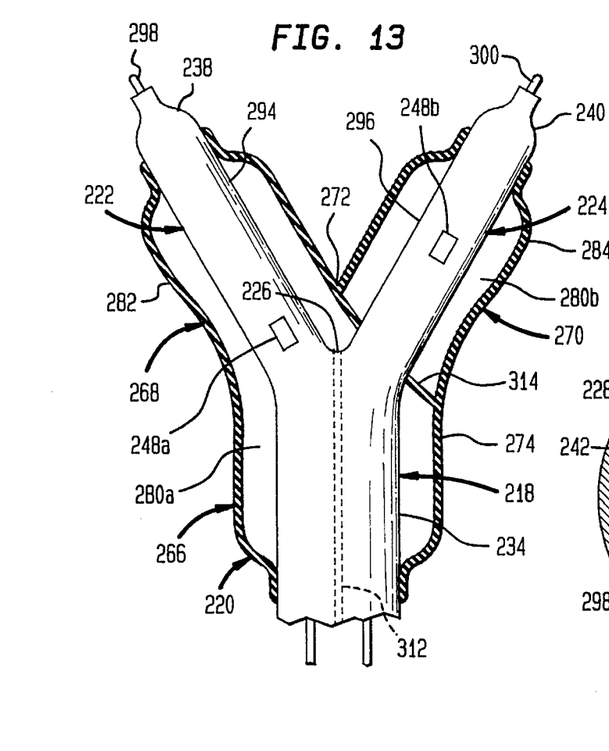
FIG. 13 is a cross-sectional view, taken along section line XIII—XIII of FIG. 12 and looking in the direction of the arrows, of the dilating catheter shown in FIG. 12, a portion of the dilating catheter being shown unsectioned to facilitate consideration and discussion.
Figure 14:
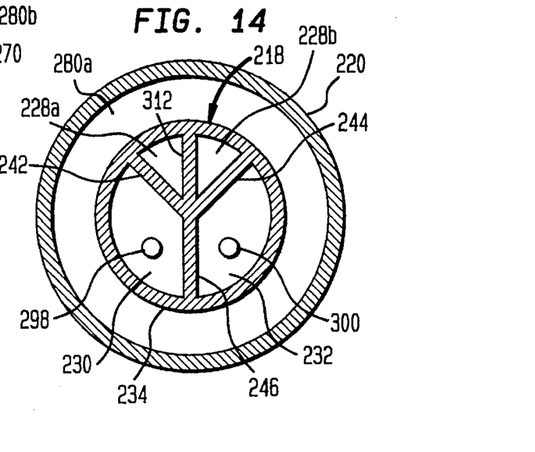
FIG. 14 is a cross-sectional view, taken along section line XIV—XIV of FIG. 12 and looking in the direction of the arrows, of the dilating catheter shown in FIG. 12.

Referring to FIG. 11, the proximal end 236 of the carrier tube 218 is attached to a connector 254 having a pair of channels 256a, 256b, the channel 256a communicating with the lumen 228a in a pressure-tight manner and the channel 256b communicating with the lumen 228b in a pressure-tight manner. The channels 256a, 256b are connected to pumps 256a, 256b, respectively, via pressure measuring devices 260a, 260b, respectively, for purposes to be discusses hereinafter.

A balloon 220, which is attached to the carrier tube 218 in the same manner as discussed in connection with FIGS. 1–4, includes a divider 314 about a bifurcation point 272 (see FIG. 13) thereof. The divider 314 divides a space 280a, which is formed between the carrier tube 218 and a trunk section 266 of the balloon 220 and between the branch extension 222 and a branch section 268 of the balloon 220, from a space 280b, which is formed between the branch extension 224 and a branch section 270 of the balloon 220 such that the space 280a is sealed in a pressure-tight manner from the space 280b. The space 280a is in communication the lumen 228a via the opening 248a while the space 280b is in communication with the lumen 228b via the opening 248b.

In performing a PTCA procedure with the catheter system 210 of FIGS. 11–14 at the stenosed bifurcated region shown in FIG. 5, with the balloon 220 being in a deflated state, the dilating catheter 214 is guided to the stenosed region in the same manner as the dilating catheter 14 of FIGS. 1–4. With the trunk section 266 properly positioned within the stenosed segment of the left main coronary artery 106 and the branch sections 268, 270 of the balloon 220 properly positioned within the stenosed segments of the left circumflex branch 108 and the left anterior descending branch 110, respectively, the trunk section 266 and the branch sections 268, 270 are simultaneously inflated to their predetermined sizes by simultaneously delivering pressurized fluid from the pump 258a to the space 280a through the lumen 228a via the opening 248a and from the pump 258b to the space 280b through the lumen 228b via the opening 248b.

It should be appreciated thin the catheter system 210 of FIGS. 11–14 provides additional advantages in addition to the ones discussed in connection with the catheter system 10 of FIGS. 1–4. For instance, because pressurized fluid is delivered to the spaces 280a, 280b by separate lumens 228a, 228b, respectively, and the delivery of pressurized fluid to the spaces 280a, 280b is independently controlled by separate pumps 258a, 258b, each space can be selectively and independently inflated to a desired pressure. Thus, for example, if only the left anterior descending branch 110 of FIG. 5 is stenosed and needs to be dilated while the artery 106 and the circumflex branch 108 do not, only the branch section 270 of the balloon 220 can be inflated to treat the stenosis in the branch 110. Alternatively, the branch section 268 and the trunk section 266 may be partially inflated, thereby preventing the branch 108 from inadvertent closure while the branch 110 is being fully dilated. In addition, the trunk section 266 and the branch section 268 can be simultaneously and fully inflated to their predetermined sizes by delivering pressurized fluid to the space 280a while the branch section 270 of the balloon 220 is or, alternatively, is not partially inflated.

It should be noted that th6 catheter system 210 and the method for performing a PTCA procedure using the catheter system 210 can include many variations and modifications in addition to the ones discussed in connection with the system 10 of FIGS. 1–4. For example, a single pump may be utilized together with suitable valving for conveying pressurized fluid to both of the lumens 228a, 228b. In addition, the balloon 220 may include another divider separating the space 280a into a sub-space formed within the branch section 268 of the balloon 220 and a sub-space formed within the trunk section 266 of the balloon, thereby providing a total of three interior spaces. In such a case, the carrier tube 218 may include an additional lumen such that pressurized fluid can be independently and selectively delivered to each of the spaces. In this way, the trunk section 266 and the branch sections 282, 284 of the balloon 220 can be selectively and independently controlled and inflated to a desired pressure. Further, the balloon 220 may have a construction other than a unitary construction.

Referring to FIG. 15, a catheter system 410, which is constructed and used in the same manner as the catheter system 10 of FIGS. 1–4 except as specified hereinafter, includes a dilating catheter 412 having branch extensions 422a, 422b, 422c, 422d of carrier tube 418, corresponding branch sections 468a, 468b, 468c, 468d of a balloon 420 and corresponding guidewires 502a, 502b, 502c, 502d. The carrier tube 418 includes a lumen (not shown) in fluid communication with a space 480 formed within the balloon 420 for receiving pressurized fluid to inflate the balloon 420. Alternatively, the carrier tube 418 may include five lumens, each of which is independently in fluid communication with one of the spaces formed within the branch sections 468a, 468b, 468c, 468d and within the trunk section 466, each of the spaces being independently and selectively inflatable. The carrier tube 418 also includes lumens 430a, 430b, 430c, 430d providing passageways for the guidewires 502a, 502b, 502c, 502d, respectively.

In FIG. 15, the dilating catheter 414 is routed to and positioned within an arch of an aorta in the same manner as discussed in connection with FIGS. 5–10 except that more guidewires are utilized in guiding the dilating catheter 414 to the stenosed region. More particularly, with the guidewires 502a, 502b, 502c, 502d extending through branches 508a, 508b, 508c, 508d, respectively, of the arch of the aorta, the branch sections 468a, 468b, 468c, 468d, respectively, are positioned within the branches 508a, 508b, 508c, 508d, respectively. The balloon 420 is so shaped and sized that when it is fully inflated it has a predetermined shape and size which are substantially similar to the shape and size of the arch of the aorta shown in FIG. 15. In this way, stenosis formed within the arch of the aorta can be treated safely and effectively.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

I claim:

1. A catheter system adapted for dilating a preselected stenosed region of a blood vessel having a first branch vessel and a second branch vessel to facilitate blood flow therethrough, comprising an inflatable member having a first branch portion and a second branch portion; carrying means for carrying said inflatable member through the vessel, said carrying means including an elongated tube provided with a proximal end and a distal end, said distal end including a first branch extension, which is attached to said first branch portion of said inflatable member, and a second branch extension, which is attached to said second branch portion of said inflatable member; guiding means for providing a guide along which said inflatable member can be routed through the vessel to the stenosed region such that said first branch portion and said second branch portion are independently and simultaneously positioned in the first branch vessel and the second branch vessel, respectively, while said inflatable member is deflated; and inflating means for inflating at least a portion of said inflatable member such that said at least a portion of said inflatable member comes into direct contact with walls of the vessel, whereby the vessel is dilated facilitating blood flow therethrough, said inflatable member being attached to said distal end of said tube such that a pressure-tight space is formed between said inflatable member and said tube to receive pressurized fluid for inflating said at least a portion of said inflatable member.

2. The system of claim 1, wherein said inflating means includes conveying means for conveying pressurized fluid from a source of pressurized fluid to said space at a pressure selected to dilate the vessel.

3. The system of claim 2, wherein said tube includes a first lumen extending therethrough from said proximal end thereof to said first branch extension and a second lumen extending therethrough from said proximal end thereof to said second branch extension.

4. The system of claim 3, wherein said guiding means includes a first guidewire and a second guidewire extending through said first lumen and said second lumen, respectively.

5. The system of claim 4, wherein said conveying means includes a third lumen extending through said tube from said proximal end thereof to said space, said third lumen communicating with a source of pressurized fluid and said space.

6. The system of claim 5, wherein said conveying means further includes an opening in said tube, said opening communicating with said space and said third lumen to allow pressurized fluid to be delivered to said space from said third lumen.

7. The system of claim 6, wherein said space is divided into a first chamber and a second chamber.

8. The system of claim 7, wherein said third lumen is in communication with said source of pressurized fluid and said first chamber through said opening in said tube.

9. The system of claim 8, wherein said conveying means further includes a fourth lumen extending through said tube from said proximal end thereof to said second chamber of said space, said fourth lumen communicating with said source of pressurized fluid and said second chamber.

10. The system of claim 9, wherein said conveying means further includes another opening in said tube, said another opening communicating with said second chamber and said fourth lumen to allow pressurized fluid to be delivered to said second chamber from said fourth lumen.

11. The system of claim 10, wherein said source of pressurized fluid includes a first pump connected to said third lumen and a second pump connected to said fourth lumen.

12. A catheter system adapted for dilating a branched region of a hollow passageway, comprising an inflatable member having a first branch portion and a second branch portion; carrying means for carrying said inflatable member through the passageway; inflating means for independently and selectively inflating said first and said second branch portions; and guiding means for providing a guide along which said inflatable member can be routed through the passageway to the branched region thereof.

13. The system of claim 12, wherein said inflating means includes first conveying means for conveying pressurized fluid to a first pressure-tight space formed within said first branch portion and second conveying means for conveying pressurized fluid to a second pressure-tight space formed within said second branch portion.

14. The system of claim 13, wherein said carrying means includes an elongated tube having a distal end and a proximal end, said inflatable member being attached to said distal end of said tube.

15. The system of claim 14, wherein said first conveying means includes a first lumen extending through said tube from said proximal end thereof to said first space.

16. The system of claim 15, wherein said second conveying means includes a second lumen extending through said tube from said proximal end thereof to said second space.

17. The system of claim 16, wherein said first conveying means further includes a first opening provided in said tube, said first opening communicating with said first lumen and said first space, and said first lumen providing a conduit for conveying pressurized fluid from a source of pressurized fluid to said first space through said first lumen and said first opening.

18. The system of claim 17, wherein said second conveying means further includes a second opening provided in said tube, said second opening communicating with said second lumen and said second space, and said second lumen providing a conduit for conveying pressurized fluid from a source of pressurized fluid to said second space through said second lumen and said second opening.

19. The system of claim 18, wherein said distal end of said tube includes a first branch extension and a second branch extension, said first branch portion of said inflatable member being attached to said first branch extension of said tube, and said second branch portion of said inflatable member being attached to said second branch extension of said tube.

20. The system of claim 19, wherein said guiding means includes a first guidewire extending through said tube and through said first branch extension and a second guidewire extending through said tube and through said second branch extension.

21. The system of claim 20, wherein said first guidewire extends through a third lumen of said tube and said second guidewire extends through a fourth lumen of said tube, said third lumen extending from said proximal end of said tube to said first branch extension and said fourth lumen extending from said proximal end of said tube to said second branch extension.

22. The system of claim 18, wherein said inflatable member includes a trunk portion and wherein said guiding means guides said trunk portion to a trunk of the branched region.

23. The system of claim 20, wherein said trunk portion of said inflatable member is selectively inflatable independently of both of said first and second branch portions.

24. The system of claim 22, wherein said trunk portion of said inflatable member is inflatable conjointly with one of said first and second branch portions.

25. A method for dilating a preselected region of a hollow passageway having first and second branches using a catheter system, which includes an inflatable member having a first branch portion and a second branch portion, said method comprising the steps of inserting the inflatable member into the passageway; routing the inflatable member to the preselected region through the passageway; independently positioning the first branch portion and the second branch portion in the first and second branches, respectively, while the inflatable member is deflated; and independently and selectively inflating the first and second branch portions of the inflatable member such that at least a portion of the inflatable member comes into direct contact with walls of the passageway, whereby the passageway is dilated.

26. The method of claim 25, wherein said inflating step includes sequentially inflating the first branch portion and the second branch portion.

27. The method of claim 25, wherein said inflating step includes simultaneously inflating the first branch portion and the second branch portion.

28. The method of claim 25, wherein the hollow passageway is a blood vessel.

29. A method for dilating a preselected region of a hollow passageway having first and second branches using a catheter system, which includes an inflatable member having a first branch portion and a second branch portion, said method comprising the steps of inserting the inflatable member into the passageway; routing the inflatable member to the preselected region through the passageway; independently positioning the first branch portion and the second branch portion in the first and second branches, respectively, while the inflatable member is deflated; and selectively inflating a trunk portion of the inflatable member independently of both of the first and second branch portions such that at least a portion of the inflatable member comes into direct contact with walls of the passageway, whereby the passageway is dilated.

30. The method of claim 29, wherein said inflating step includes inflating the trunk portion conjointly with one of said first and second branch portions.

31. A method for dilating a preselected region of a hollow passageway having first and second branches using a catheter system, which includes an inflatable member having a first branch portion and a second branch potion, said method comprising the steps of inserting the inflatable member into the passageway; routing the inflatable member to the preselected region through the passageway; independently positioning the first branch portion and the second branch portion in the first and second branches, respectively, while the inflatable member is deflated; and inflating the second branch portion fully while inflating the first branch portion partially such that at least a portion of the inflatable member comes into direct contact with walls of the passageway, whereby the passageway is dilated.

* * * * *